United States Patent
Bovo et al.

(10) Patent No.: US 11,283,024 B2
(45) Date of Patent: Mar. 22, 2022

(54) ORGANIC PHOTODETECTOR WITH REDUCED DARK CURRENT

(71) Applicant: Cambridge Display Technology Limited, Godmanchester (GB)

(72) Inventors: Gianluca Bovo, Godmanchester (GB); Nir Yaacobi-Gross, Godmanchester (GB)

(73) Assignee: Cambridge Display Technology Limited, Godmanchester (GB)

( * ) Notice: Subject to any disclaimer, the term of this patent is extended or adjusted under 35 U.S.C. 154(b) by 327 days.

(21) Appl. No.: 16/071,842

(22) PCT Filed: Jan. 16, 2017

(86) PCT No.: PCT/GB2017/050095
§ 371 (c)(1),
(2) Date: Jul. 20, 2018

(87) PCT Pub. No.: WO2017/125719
PCT Pub. Date: Jul. 27, 2017

(65) Prior Publication Data
US 2021/0013417 A1    Jan. 14, 2021

(30) Foreign Application Priority Data

Jan. 21, 2016 (GB) ..................... 1601151
Oct. 20, 2016 (GB) ..................... 1617753

(51) Int. Cl.
*H01L 51/00*      (2006.01)
*C07C 69/618*    (2006.01)
*H01L 51/42*      (2006.01)

(52) U.S. Cl.
CPC ........ *H01L 51/0047* (2013.01); *C07C 69/618* (2013.01); *C07C 2604/00* (2017.05); *H01L 51/4253* (2013.01)

(58) Field of Classification Search
None
See application file for complete search history.

(56) References Cited

U.S. PATENT DOCUMENTS

2012/0261649 A1   10/2012   Kim et al.
2014/0054442 A1   2/2014   Huang et al.
(Continued)

FOREIGN PATENT DOCUMENTS

JP    2012-502495 A    1/2012
JP    2017-502158 A    1/2017
(Continued)

OTHER PUBLICATIONS

International Search Report and Written Opinion for International Application No. PCT/GB2017/050095, dated Mar. 16, 2017.
(Continued)

*Primary Examiner* — Long Pham
(74) *Attorney, Agent, or Firm* — Wolf, Greenfield & Sacks, P.C.

(57) ABSTRACT

An organic photodetector comprising a first electrode, a second electrode, and a photosensitive organic layer between the electrodes, the photosensitive organic layer comprising a donor polymer and an acceptor compound, characterized in that the acceptor compound has a LUMO level shallower than that of the fullerene derivative PCBM.

13 Claims, 5 Drawing Sheets

(56) References Cited

U.S. PATENT DOCUMENTS

| | | | |
|---|---|---|---|
| 2014/0319461 A1 | 10/2014 | Park et al. | |
| 2020/0243770 A1* | 7/2020 | Park | C08G 61/126 |
| 2021/0013417 A1* | 1/2021 | Bovo | C07C 69/618 |
| 2021/0043689 A1* | 2/2021 | Tokuhara | H04N 5/369 |

FOREIGN PATENT DOCUMENTS

| | | |
|---|---|---|
| JP | 2017-506426 A | 3/2017 |
| WO | WO 2011/160021 A2 | 12/2011 |
| WO | WO 2013/135339 A2 | 9/2013 |
| WO | WO 2015/067335 A1 | 5/2015 |
| WO | WO 2015/067336 A2 | 5/2015 |

OTHER PUBLICATIONS

Combined Search and Examination Report for British Application No. 1601151.2, dated Jul. 20, 2016.

Backer et al., High efficiency organic photovoltaics incorporating a new family of soluble fullerene derivatives. Chemistry of Materials. 2007;19(12):2927-9.

He et al., Novel fullerene acceptors: synthesis and application in low band gap polymer solar cells. Electronic Supplementary Information (ESI) available: experimental details including the polymer synthesis, the fabrication and characterization of the polymer solar cells, measurements, and instruments. Journal of Materials Chemistry. 2012;22(26):13391-4. DOI: 10.1039/c2jm31712e.

Hide et al., Polymer diodes using poly(3,4-dicyanothiophene). Synthetic Metals. 1997;85:1255-6.

Jahnel et al., Integration of near infrared and visible organic photodiodes on a complementary metal-oxide-semiconductor compatible backplane. Thin Solid Films. 2015;592:94-8.

Larson et al., Electron Affinity of Pheryl-C 61-butyric acid methyl ester (PCBM). Journal of Physical Chemistry C. 2013;117(29):14958-64.

Japanese communication dated Sep. 8, 2020 in connection with Japanese Application No. 2018-537763.

Baeg et al., Organic light detectors: photodiodes and phototransistors. Advanced Materials. Aug. 21, 2013;25(31):4267-95.

Verilhac, Recent Developments of solution-processed organic photodetectors. Proceeding of 2012 International Semiconductor Conference Dresden-Grenoble (ISCDG). 2012. pp 101-106.

Japanese communication dated May 18, 2021 in connection with Japanese Application No. 2018-537763.

European communication dated Jun. 18, 2021 in connection with European Application No. 17700741.6.

* cited by examiner

ORGANIC PHOTODETECTOR WITH REDUCED DARK CURRENT

RELATED APPLICATIONS

This application is a national stage filing under 35 U.S.C. 371 of International Patent Application Serial No. PCT/GB2017/050095, filed Jan. 16, 2017 which claims priority to United Kingdom application numbers GB 1601151.2, filed Jan. 21, 2016 and GB 1617753.7, filed Oct. 20, 2016, each of which is incorporated herein by reference in their entirety.

BACKGROUND TO THE INVENTION

This invention relates to organic photodiodes for use as photodetectors. It relates specifically, though not exclusively, to organic photodiodes having an active layer comprising an electron acceptor material and an electron donating material.

Fullerene derivatives are the most common electron acceptor material for organic bulk heterojunction solar cells since they act as a good electron acceptor and exhibit high electron mobility.

SUMMARY OF THE INVENTION

According to the present invention there is provided an organic photodetector as specified in claim 1. According to another aspect of the present invention there is provided the use of a compound as specified in claim 2.

Prior art describes the use of alternative fullerene derivatives in organic photovoltaic devices (OPVs) as a method to control exciton dissociation and increase open circuit voltage.

Here we show the use of the same fullerene derivatives in order to reduce dark currents in organic photodiodes while maintaining high quantum efficiency (~90% of control sample). As a results the detector Specific detectivity (D*) is increased.

DETAILED DESCRIPTION OF SPECIFIC EMBODIMENTS

The LUMO energy level of fullerene derivatives is highly dependent on the fullerene sidechain originally needed to allow solubility in organic solvents. Table 1 presents the C60 based fullerene derivatives used in the present embodiments and their corresponding LUMO levels.

TABLE 1

| Material | Structure | LUMO (eV) |
|---|---|---|
| PCBM (Comparative) | 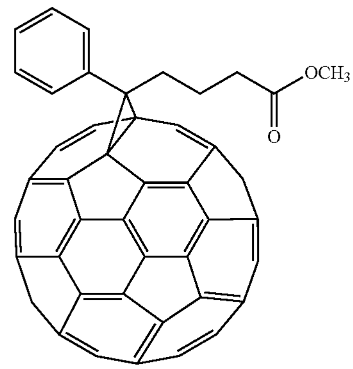 [SMILES: COC(=O)CCCC1(c2ccccc2)C23C=Cc4cc5c6c7c4C21c1c2c4c(cc8ccc9cc(c6c6c9c8c4c6c17)C5)CC2=C3] | −3.80 |
| IPB (R = butyl) | R is butyl | −3.78 |
| bisPCBM | 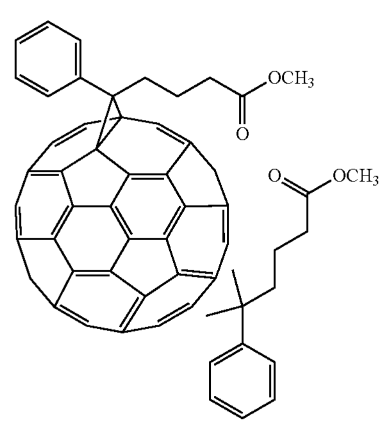 | −3.69 |

TABLE 1-continued

| Material | Structure | LUMO (eV) |
|---|---|---|
| ICBA | (fullerene derivative structure) | −3.61 |

In use, photodetectors as described herein are connected to a voltage source for applying a reverse bias to the device and a device configured to measure photocurrent. A high dark current in photodetectors limits the detectible optical input signal.

By reducing the dark current the detector Specific detectivity (D*) is increased as can be seen from equation 1:

$$D^* = \frac{R}{\sqrt{2qJ_{dark}}}$$

Where R is the OPD responsivity expressed in [A/W] and q is the electron charge.

Figure 1:
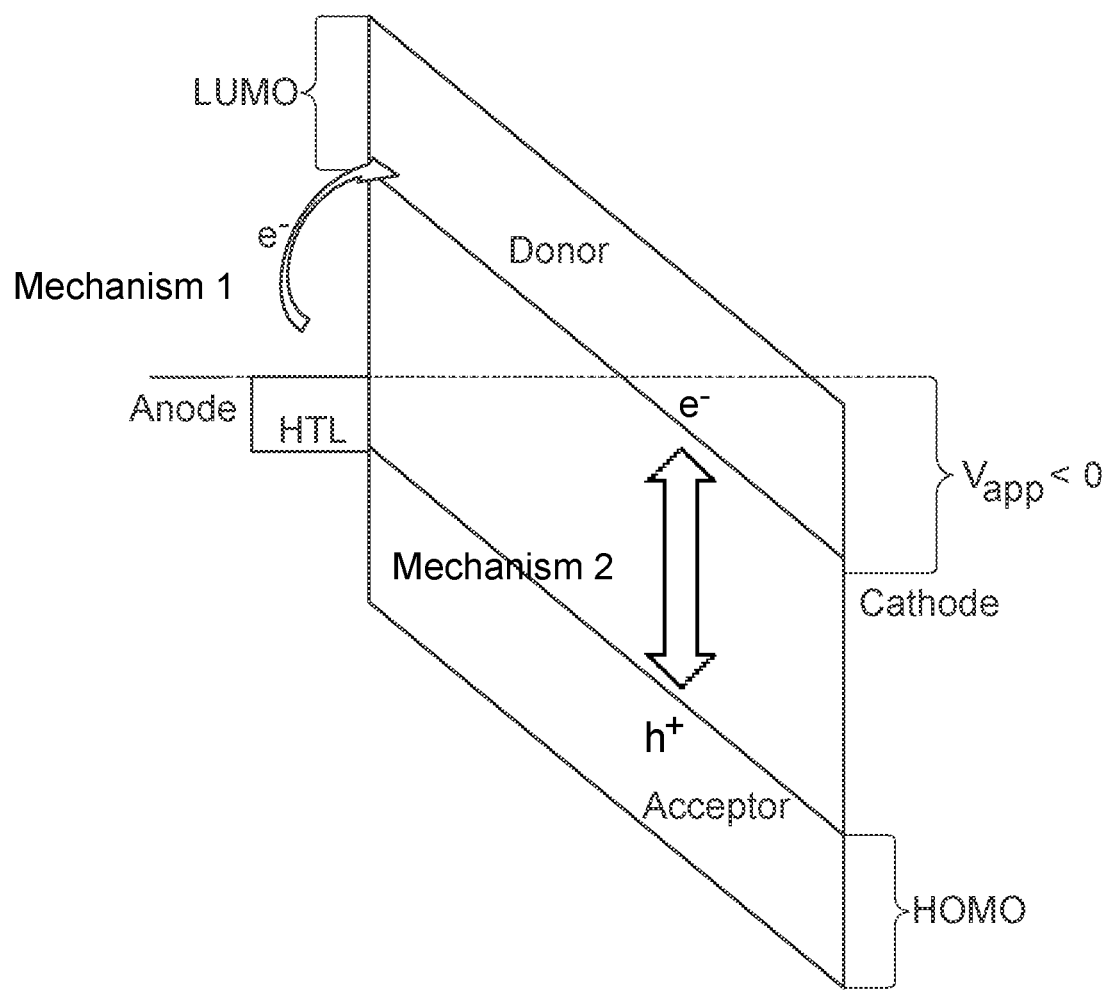
FIG. 1 shows an energy level diagram illustrating the energy level offset between the anode or hole transport layer (HTL) and the acceptor LUMO under reverse bias in a device according to the present invention.

One of the mechanism contributing to the non-desired dark current in organic photodiodes (OPD) is electron injection from the diode anode to the acceptor LUMO. This injection mechanism is strongly dependent on the energy level offset between the work function of the anode (or if a hole transport layer is present the LUMO of a hole transporting material in the hole transport layer (HTL)) and the acceptor LUMO. (see mechanism 1 in FIG. 1).

Another mechanism that contributing to the dark current is the energy gap between the acceptor LUMO and the Donor HOMO (also known as the charge-transport "CT state"). Thermal generation across this energy gap give rise to the dark current. (see mechanism 2 in FIG. 1).

Both mechanisms are dependent on the acceptor LUMO level. Therefore replacing the commonly used PCBM with a fullerene derivative having shallower LUMO level reduces the device dark current. The inventors have discovered that this injection mechanism is strongly dependent on the energy level offset between the work function of the anode or LUMO level of the hole transport layer (HTL) and the acceptor LUMO (see FIG. 1).

Figure 2:
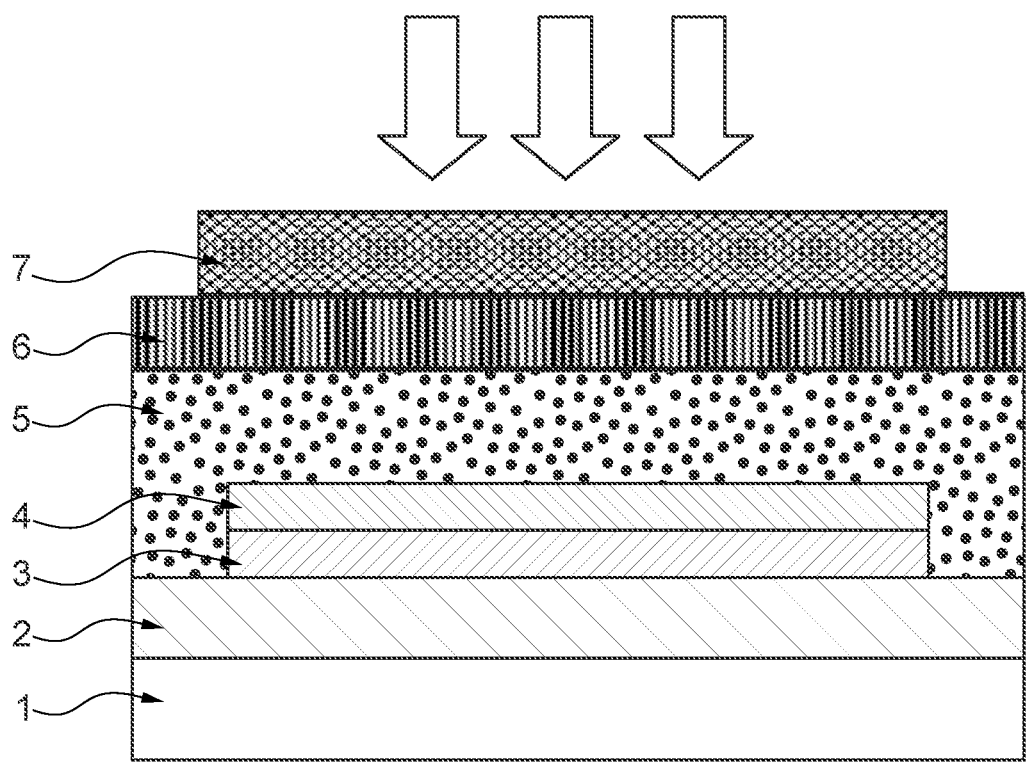
FIG. 2 shows a device structure according to the present invention.

FIG. 2 presents an example device structure that was used to demonstrate the effect of fullerene derivative variation on dark currents. A reflective layer of silver or an alloy (2) is provided on a glass substrate (1). On this layer a layer of ITO (3) is deposited by physical vapour deposition. A 5 nm thick e-modifier layer (4) is deposited on top of the ITO layer. An organic photosensitive layer (5) is then deposited onto the structure from solution. In the present case it was 350 nm thick and deposited by spin coating, but other deposition methods can be used as an alternative. The solution comprised 1 part polymer as described below to 2 parts of the fullerene derivative by weight. The solution had a total solids content of 3% by weight, and the solvent used was 90% 1,2,4 trimethylbenzene with 10% benzyl benzoate.

The donor (i.e. p-type) OSC used in the embodiments is a polymer having a structure as shown below:

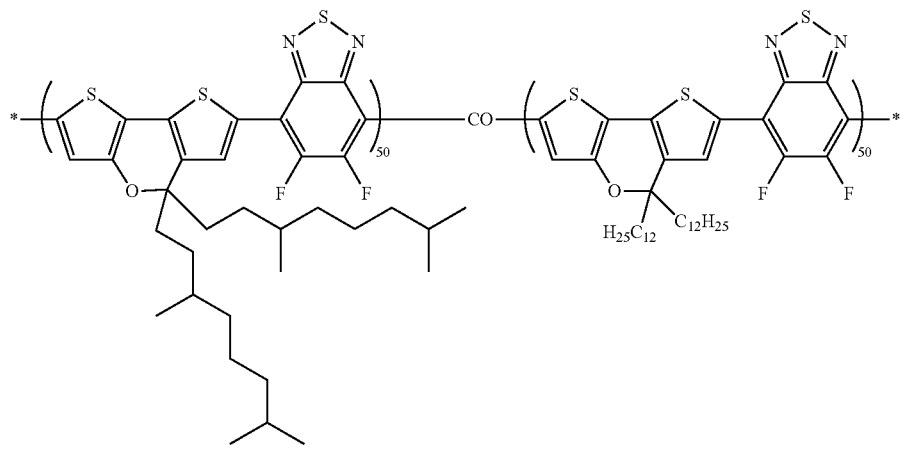

The p type OSC used is not particularly limited and may be appropriately selected from standard electron donating materials that are known to the person skilled in the art and are described in the literature, including organic polymers, oligomers and small molecules. In a preferred embodiment the p-type OSC comprises an organic conjugated polymer, which can be a homopolymer or copolymer including alternating, random or block copolymers. Preferred are non-crystalline or semi-crystalline conjugated organic polymers. Further preferably the p-type organic semiconductor is a conjugated organic polymer with a low bandgap, typically between 2.5 eV and 1.5 eV, preferably between 2.3 eV and 1.8 eV. As exemplary p-type OSC polymers, polymers selected from conjugated hydrocarbon or heterocyclic polymers including polyacene, polyaniline, polyazulene, polybenzofuran, polyfluorene, polyfuran, polyindenofluorene, polyindole, polyphenylene, polypyrazoline, polypyrene, polypyridazine, polypyridine, polytriarylamine, poly(phenylene vinylene), poly(3-substituted thiophene), poly(3,4-bisubstituted thiophene), polyselenophene, poly(3-substituted selenophene), poly(3,4-bisubstituted selenophene), poly(bisthiophene), poly(terthiophene), poly(bisselenophene), poly(terselenophene), polythieno[2,3-b]thiophene, polythieno[3,2-b]thiophene, polybenzothiophene, polybenzo[1,2-b:4,5-b]dithiophene, polyisothianaphthene, poly(monosubstituted pyrrole), poly(3,4-bisubstituted pyrrole), poly-1,3,4-oxadiazoles, polyisothianaphthene, derivatives and co-polymers thereof may be mentioned. Preferred examples of p-type OSCs are copolymers of polyfluorenes and polythiophenes, each of which may be substituted, and polymers comprising benzothiadiazole-based and thiophene-based repeating units, each of which may be substituted. It is understood that the p-type OSC may also consist of a mixture of a plurality of electron donating materials.

Other fullerene derivatives having a shallower LUMO level than PCBM can be used as alternative acceptor compounds. Several suitable materials are disclosed in U.S. Pat. No. 8,952,249 and in Koositra et al. Org. Lett. [2007] volume 9, issue 4 pages 551-554. The compounds are not limited to C60 materials, and for example C70, C84 or higher derivatives and mixtures could be used as an alternative.

Other alternative acceptor compounds are, for example, IPH and ICMA. The structure and LUMO levels of these materials are shown below:

| Material | Structure | LUMO |
|---|---|---|
| IPH (R = hexyl) | R is hexyl | -3.75 eV |
| ICMA | 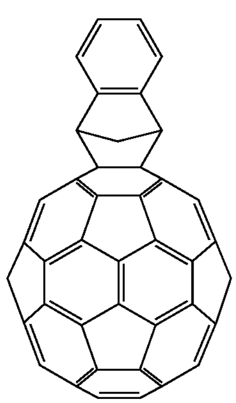 | -3.78 eV |

Optionally, the fullerene is selected from fullerenes of formulae (Ia), (Ib) and (Ic):

(Ia)

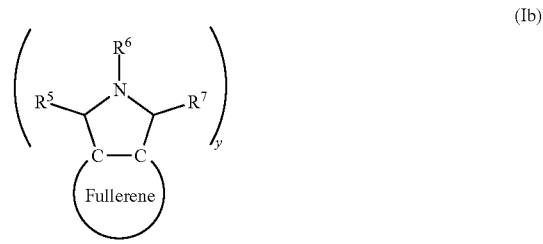

(Ib)

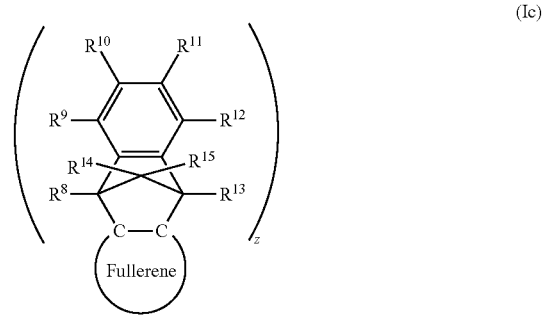

(Ic)

wherein Fullerene is selected from $C_{60}$, $C_{70}$, $C_{76}$, $C_{78}$, $C_{84}$ and $C_{96}$ fullerene; x is 2; y is 1 or 2; z is 1 or 2; and $R^4$-$R^{15}$ are each independently H or a substituent.

Substituents $R^4$-$R^{15}$ are optionally and independently in each occurrence selected from the group consisting of aryl or heteroaryl, optionally phenyl, which may be unsubstituted or substituted with one or more substituents; and branched, linear or cyclic $C_{1-20}$ alkyl wherein one or more non-adjacent, non-terminal C atoms may be replaced with O, S, CO or COO and one or more H atoms may be replaced with F.

Substituents of aryl or heteroaryl, where present, are optionally selected from $C_{1-12}$ alkyl wherein one or more non-adjacent, non-terminal C atoms may be replaced with O, S, CO or COO and one or more H atoms may be replaced with F.

By "non-terminal C atom" of an alkyl as used herein is meant the methyl group of a linear alkyl or the methyl groups of a branched alkyl.

A preferred acceptor compound is a compound of formula (Id):

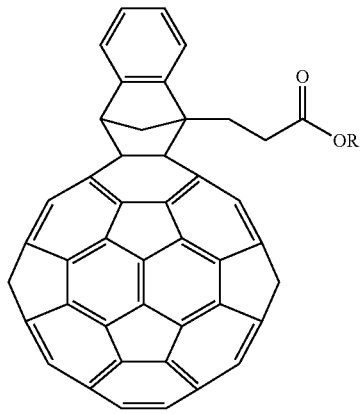

(Id)

wherein R is a branched, linear or cyclic $C_{1-12}$ alkyl group, preferably a linear or branched $C_4$-$C_7$ alkyl (butyl, pentyl, hexyl or heptyl) group.

Onto the photosensitive layer (5) a hole injection layer (HiL) (6) was deposited. This layer was 40 nm thick and consisted of Plexcore CA2004 (available commercially from Solvay/Plextronics Inc.). On top of the structure a semi-transparent anode (7) was deposited having a thickness of 100 nm or less. Typically 5 to 100 nm. 100 nm was used in the embodiments.

We note that this invention is not limited to this device structure or material selection.

Figure 3:
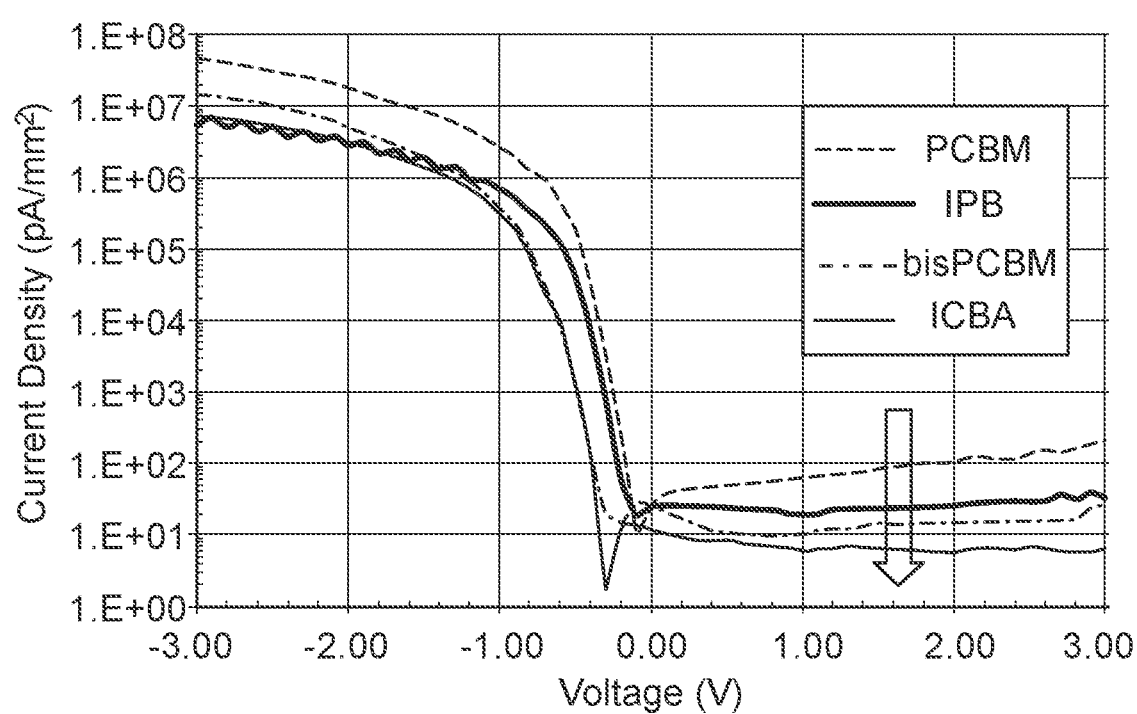
FIG. 3 shows the dark current density-voltage curves of four organic photodetectors fabricated from polymer:fullerene blends made from four different fullerene derivatives.

FIG. 3 illustrates the dark current density-voltage curves of four photodiodes fabricated from polymer:fullerene blends made from the four different fullerene derivatives described in Table 1.

Figure 4:
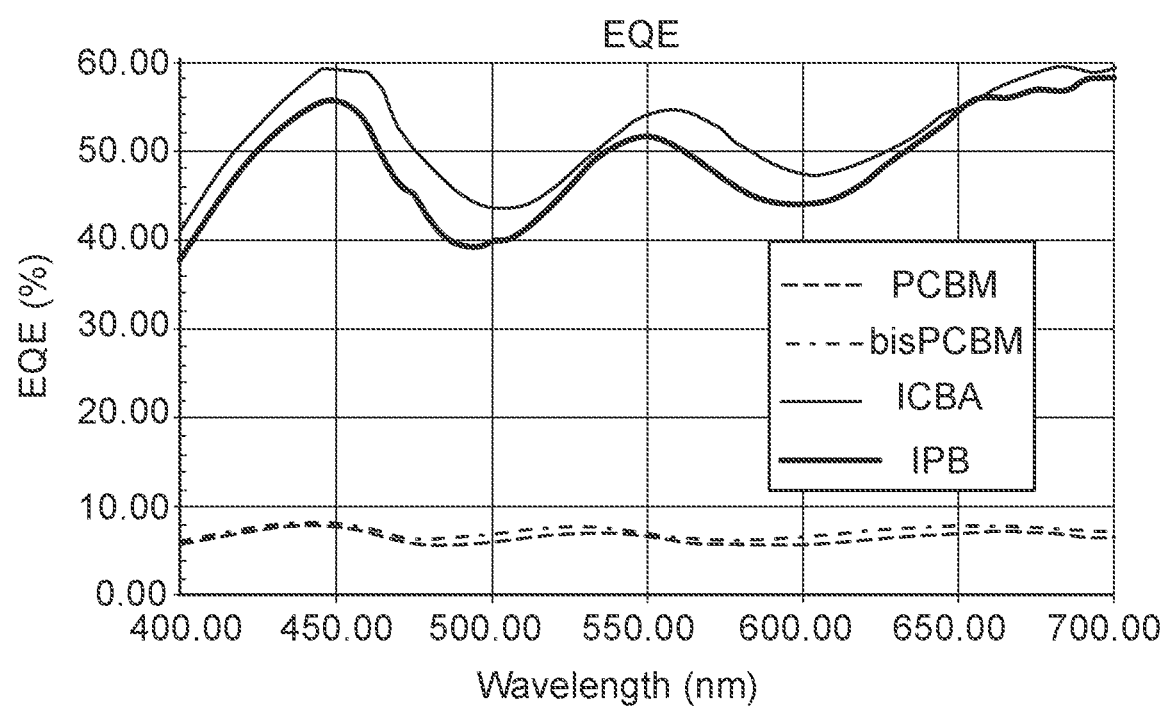
FIG. 4 shows the external quantum efficiency of the four organic photodetectors under −1 V reverse bias fabricated from polymer:fullerene blends made from four different fullerene derivatives.

FIG. 4 presents the above devices EQE. As can be clearly seen the there is a strong dependence of EQE with the fullerene LUMO level. Large shift in the Acceptor LUMO can lead to inefficient device as the donor acceptor offset is insufficient for exciton dissociation. Nevertheless, it can also be seen that an optimal shift (IPB) can lead to dark current redaction while maintaining high EQE (~90% of reference PCBM).

Figure 5:
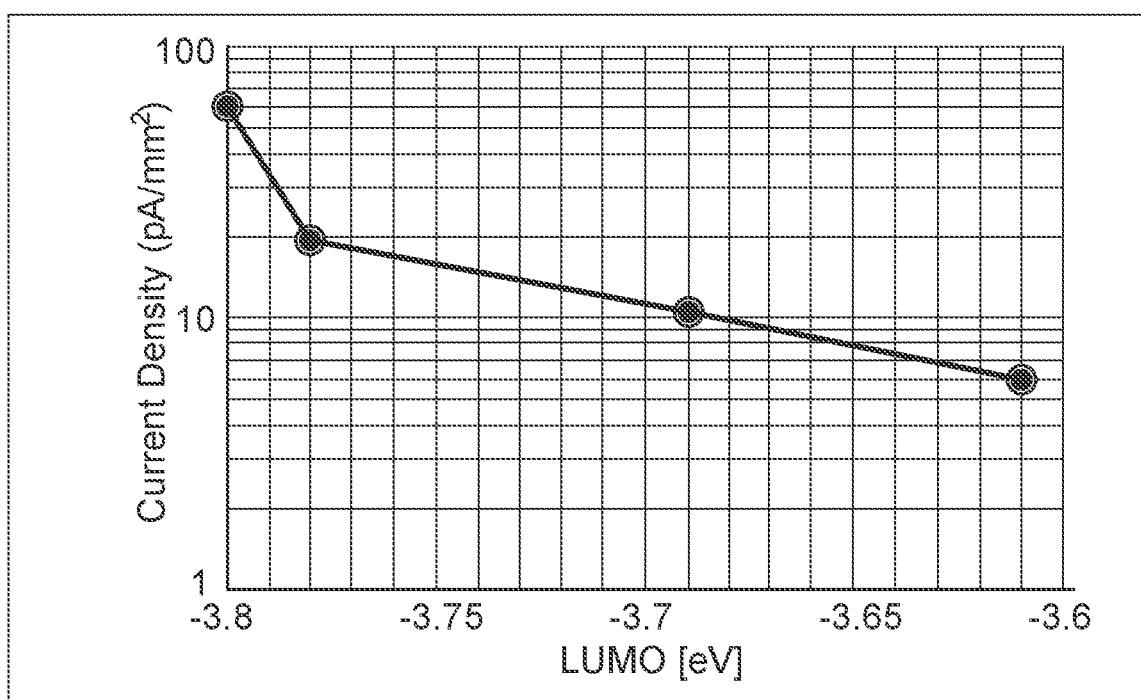
FIG. 5 shows the correlation between the dark current at −1V reverse bias and the fullerene LUMO level.

Finally FIG. 5 presents the correlation between the dark current at –1V reverse bias and the fullerene LUMO level.

Although shallower LUMO materials have been used in solar cells to increase Voc and hence the solar cell figure of merit, in general shallower LUMO materials in solar cells will not provide significantly lower leakage current. This is because the devices typically have a large shunt resistance in parallel with the diode which masks the dark current with an additional leakage current in parallel. The reduction in dark current produced by using an electron acceptor material with a shallower LUMO will only be observed if care is taken to minimise such parasitic parallel resistances. Such care is taken with photodetectors as the figure of merit for a photodetector is inversely proportional to the square root of the dark current as shown above in equation 1.

Dark current density was measured from –3V to 3V with 0.05V steps using Keithley 2400 source-meter.

EQE was measured under –1V reverse bias using the following setup:

Xenon lamp coupled to ¼ meter monochromator (Oriel Cornerstone) and filter wheel.

The device current was measured using Keithley electrometer.

The device photocurrrent was calculated by reducing the device dark current from the total current.

The EQE was calculated using the following equation 2:
$EQE = R \cdot hc/\lambda$ where R is responsivity in A/W, h is the Planck constant, c the speed of light, and $\lambda$ is the excitation wavelength.

The excitation power which is required to calculate the responsivity R is measured using a calibrated Si photodiode.

HOMO and LUMO levels as described anywhere herein may be measured by square wave voltammetry (SWV) at room temperature. In Squarewave Voltammetry, the current at a working electrode is measured while the potential between the working electrode and a reference electrode is swept linearly in time. The difference current between a forward and reverse pulse is plotted as a function of potential to yield a voltammogram.

The apparatus to measure HOMO or LUMO energy levels by SWV may comprise a cell containing tertiary butyl ammonium perchlorate or tertiary butyl ammonium hexafluorophosphate in acetonitrile; a glassy carbon working electrode; a platinum counter electrode and a leak free Ag/AgCl reference electrode.

Ferrocene is added directly to the existing cell at the end of the experiment for calculation purposes where the potentials are determined for the oxidation and reduction of ferrocene versus Ag/AgCl using cyclic voltammetry (CV)

Apparatus:

CHI 660D Potentiostat 3 mm diameter glassy carbon working electrode

Leak free Ag/AgCl reference electrode

Pt wire auxiliary or counter electrode 0.1M tetrabutylammonium hexafluorophosphate in acetonitrile Method:

The sample is dissolved in Toluene (3 mg/ml) and spun at 3000 rpm directly on to the glassy carbon working electrode LUMO=4.8-E ferrocene (peak to peak average)–E reduction of sample (peak maximum)

HOMO=4.8-E ferrocene (peak to peak average)+E oxidation of sample (peak maximum)

A typical SWV experiment runs at 15 Hz frequency; 25 mV amplitude and 0.004V increment steps. Results are calculated from 3 freshly spun film samples for both the HOMO and LUMO data.

All experiments are run under an Argon gas purge.

The invention claimed is:

1. An organic photodetector comprising a first electrode, a second electrode, and a photosensitive organic layer between the electrodes, the photosensitive organic layer comprising a donor p-type organic semiconductor compound and an acceptor compound, characterized in that the acceptor compound has a LUMO level shallower than the LUMO level of the fullerene derivative PCBM:

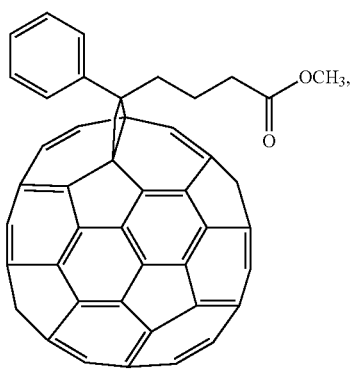

and wherein the donor p-type organic semiconductor compound is a conjugated organic polymer having a bandgap between 2.5 eV and 1.5 eV.

2. An organic photodetector as claimed in claim 1 in which the donor p-type organic semiconductor compound is a p-type polymer.

3. An organic photodetector as claimed in claim 1 in which the acceptor compound is a fullerene derivative.

4. An organic photodetector according to claim 3 in which the acceptor compound is a fullerene derivative of formula (Ia), (Ib) or (Ic):

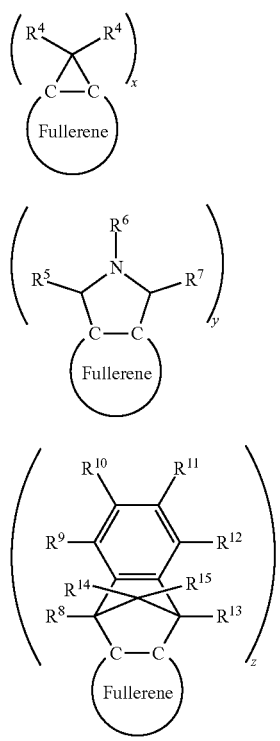

wherein Fullerene is selected from $C_{60}$, $C_{70}$, $C_{76}$, $C_{78}$, $C_{84}$ and $C_{96}$ fullerene; x is 2; y is 1 or 2; z is 1 or 2; and $R^4$-$R^{15}$ are each independently H or a substituent.

5. An organic photodetector according to claim 4 wherein $R^4$-$R^{15}$ are independently in each occurrence selected from the group consisting of H; aryl or heteroaryl which is unsubstituted or substituted with one or more substituents; and branched, linear or cyclic $C_{1-20}$ alkyl wherein one or more non-adjacent, non-terminal C atoms may be replaced with O, S, CO or COO and one or more H atoms may be replaced with F.

6. An organic photodetector as claimed in claim 1 in which the acceptor compound is a C60, C70 or C84 fullerene derivative.

7. An organic photodetector as claimed in claim 1 wherein the acceptor compound is a compound of formula (Id):

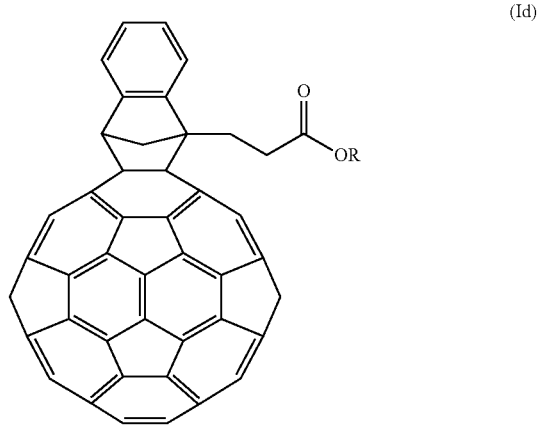

wherein R is a linear, branched or cyclic $C_{1-12}$ alkyl group.

8. An organic photodetector according to claim 7 wherein R is a linear or branched $C_{4-7}$ alkyl group.

9. An organic photodetector as claimed in claim 1 in which the acceptor compound is IPB or IPH.

10. A sensor comprising a light source and an organic photodetector according to claim 1.

11. A method of detecting light comprising measuring a photocurrent generated by light incident on an organic photodetector according to claim 1.

12. A method for reducing the dark current in a photosensitive active layer of an organic photodetector, comprising a donor p-type conjugated organic polymer having a bandgap between 2.5 eV and 1.5 eV, the method comprising use of an acceptor compound having a shallower LUMO level than the LUMO level of PCBM.

13. An organic photodetector according to claim 1, wherein the donor p-type organic semiconductor compound is a conjugated organic polymer having a bandgap between 2.5 eV and 1.5 eV.

* * * * *